United States Patent [19]

Manzer et al.

[11] Patent Number: 4,902,838

[45] Date of Patent: Feb. 20, 1990

[54] ISOMERIZATION OF SATURATED FLUOROHYDROCARBONS

[75] Inventors: Leo E. Manzer; V. N. Mallikarjuna Rao, both of Wilmington, Del.

[73] Assignee: E. I. Du Pont de Nemours and Company, Wilmington, Del.

[21] Appl. No.: 291,100

[22] Filed: Dec. 28, 1988

[51] Int. Cl.$^4$ .................... C07C 17/24; C07C 17/34
[52] U.S. Cl. .................................... 570/151; 570/156
[58] Field of Search .............................. 570/151

[56] References Cited

U.S. PATENT DOCUMENTS

| | | | |
|---|---|---|---|
| 2,598,411 | 5/1952 | Fager et al. | 260/653 |
| 3,087,974 | 4/1963 | Fainberg et al. | 260/653 |
| 3,398,202 | 8/1968 | Foulletier | 570/151 |
| 3,787,331 | 7/1974 | Groppelli et al. | 252/442 |

FOREIGN PATENT DOCUMENTS

| | | |
|---|---|---|
| 2245372 | 3/1974 | Fed. Rep. of Germany . |
| 121710 | 10/1978 | Japan ................................... 570/151 |
| 873212 | 7/1961 | United Kingdom . |

Primary Examiner—J. E. Evans

[57] ABSTRACT

A process for isomerizing saturated $C_2$ to $C_6$ fluorohydrocarbons having lesser thermodynamic stability to fluorohydrocarbons having greater thermodynamic stability comprising contacting in the gaseous phase at a temperature from about 200° C. to about 475° C. at least one $C_2$ to $C_6$ saturated fluorohydrocarbon with a catalyst composition comprising an aluminum fluoride.

12 Claims, No Drawings

ISOMERIZATION OF SATURATED FLUOROHYDROCARBONS

FIELD OF THE INVENTION

This invention relates to a catalytic process for the isomerization of fluorohydrocarbons, wherein the fluorine and hydrogen exchange places on the carbon skeleton, using a catalyst composition comprising an aluminium fluoride.

BACKGROUND OF THE INVENTION

U.S. Pat. No. 2,598,411 discloses the rearrangement of halogen atoms in perchlorofluoroalkanes by the shifting of like halogens to different carbon atoms using $AlCl_3$, $AlBr_3$, and their mixtures with antimony halides as catalysts. Carriers such as sintered aluminum fluoride or activated charcoal, on which the catalysts may be deposited, are disclosed.

GB 873,212 discloses a process for the manufacture of $CF_3CHClBr$ by shifting a fluorine atom and the bromine atom of $CF_2BrCFHCl$ using $AlCl_3$. The patent teaches that if one attempts to isomerize chlorofluorohydrocarbons with $AlCl_3$, HCl is lost and the corresponding ethylene derivative is obtained even under mild conditions.

U.S. Pat. No. 3,087,974 discloses a method of rearranging perfluorochloroethanes by contacting said perfluorochloroethanes at temperatures between 150° and 600° C. with a catalyst prepared by reacting activated alumina with a lower fluorocarbon having not more than one hydrogen atom. For example, the patent teaches that, when $CH_3CF_2Cl$ is passed over activated alumina at about 300° C., dehydrofluorination occurs and $CH_2=CClF$ is produced.

JP 53-121710 discloses the isomerization of chlorofluorocarbons containing one or two hydrogen atoms by contacting them with catalysts represented by the formula $AlCl_xF_yO_z$; where $x+y+z=3$, $0<x<3$, $0<y<3$, and $0 \leq z \leq 3/2$. In all cases only fluorine and chlorine atoms exchange positions. The isomerization is more effective, i.e., catalyst life is prolonged, in the presence of perchloro- or perchlorofluorocarbons co-feed. The highest temperature used is about 300° C. since, above this temperature, starting materials are said to be decomposed.

U.S. Pat. No. 3,787,331 discloses catalysts made from $AlF_3$ containing manganese, chromium and/or nickel which are used for the fluorination of perchlorofluorocarbon, $CF_2ClCFCl_2$ to $CF_2ClCF_2Cl$ with reduced isomerization of the starting material to $CF_3CCl_3$. More isomerization is observed when using pure $AlF_3$ as catalyst.

DT 2,245,372 discloses the preparation of di- and trifluoroethane compounds of general formula $CF_2ZCZ_3$ or $CF_3CZ_3$ in which Z=H, Cl, Br, or I, by isomerization of $CFZ_2CFZ_2$ or $CF_2ZCFZ_2$ using as catalyst a mixture of aluminum halides of the type $AlXY_2$ and $AlX_2Y$ in which X and Y are Cl, Br, or I. In one example Br and F atoms exchange places in $CF_2BrCFHCl$ to yield $CF_3CHBrCl$.

Processes for the isomerization of hydrogen containing fluorohalocarbons as discussed above are known. However, the process of the instant invention provides the isomerization of fluorohydrocarbons, compounds containing only carbon, fluorine and hydrogen atoms, wherein fluorine and hydrogen atoms exchange places on the carbon skeleton.

SUMMARY OF THE INVENTION

This invention provides a process for isomerizing saturated $C_2$ to $C_6$ fluorohydrocarbons having lesser thermodynamic stability to fluorohydrocarbons having greater thermodynamic stability comprising;

contacting in the gaseous phase at a temperature from about 200° C. to about 475° C. at least one $C_2$ to $C_6$ saturated fluorohydrocarbon with a catalyst composition comprising an aluminum fluoride.

In the isomerization process of this invention at least one fluorine atom in the saturated fluorohydrocarbon exchanges places with at least one adjacent hydrogen atom on the carbon skeleton of the saturated fluorohydrocarbon to form a more thermodynamically stable isomer of the saturated fluorohydrocarbon. The process of this invention represents the first example of an isomerization of a saturated fluorohydrocarbon wherein at least one fluorine atom and at least one hydrogen atom, located on adjacent carbon atoms of the carbon skeleton, exchange places.

DETAILS OF THE INVENTION

The saturated fluorohydrocarbons isomerized in accordance with this invention are compounds containing only carbon, hydrogen and fluorine atoms. These saturated fluorohydrocarbons are isomerized to their more thermodynamically stable isomer or isomers. By more thermodynamically stable isomers is meant those isomers with the lowest free energy of formation, as calculated using Benson's Group Contribution Method (S. W. Benson et. al., Chem. Rev., 69, 279(1969)). For example, in general thermodynamic stability in the isomer or isomer produced in accordance with this invention is favored when the fluorine/hydrogen atom exchange is such that the highest number of fluorine atoms possible exist on terminal carbon atoms, i.e., -$CF_3$.

For example, in the case of saturated fluorohydrocarbons having two carbon atoms, 1,1,2,2-tetrafluoroethane (HFC-134) is isomerized to 1,1,1,2-tetrafluoroethane (HFC-134a); 1,1,2-trifluoroethane (HFC-143) to 1,1,1,-trifluoroethane (HFC-143a); and 1,2-difluoroethane (HFC-152) to 1,1-difluoroethane (HFC-152a).

The catalyst composition utilized in the practice of this invention must contain an aluminum fluoride, which may or may not be supported. By aluminum fluoride is meant at least one of $AlF_3$ and fluorided alumina. The $AlF_3$ and/or fluorided alumina can be prepared by any method known in the art or described hereinbelow.

By fluorided alumina is meant a high fluorine-content composition comprising aluminum, oxygen, and fluorine in such proportions that the total fluorine content of the catalyst composition taken as $AlF_3$ corresponds to, preferably at least 50 weight percent, exclusive of any supported metal which may be present, and more preferably 80 weight percent.

The catalyst composition may also contain up to 50% by weight of at least one metal on a support consisting essentially of aluminum, oxygen, and fluorine in such proportions that the fluorine content of the catalyst composition corresponds to an $AlF_3$ content of, preferably, at least 50% by weight of the catalyst composition exclusive of the metal.

The remainder of the composition may include alumina or aluminum oxyfluoride. The high-AlF3-content catalyst and supported catalysts can be prepared in-situ by exhaustive HF fluorination of alumina, optionally impregnated with at least one metal compound which may be in the form of the oxide, oxyhalide, halide or pseudohalide or such other form which is convertible to the fluoride or oxyfluoride under the conditions of the fluorination pretreatment step described herein. The halides include fluorides, chlorides, or bromides. The pseudohalides include cyanides, cyanates, and thiocyanates. The total content of metal, expressed as the divalent oxide is more than 0.02% but not more than 50% by weight of the supported catalyst.

Catalysts based on fluorided alumina with or without one or more metal compounds impregnated therein are preferably prepared prior to use for the isomerization of saturated fluorohydrocarbon by treatment with a vaporizable fluorine-containing fluorinating compound, such as HF, $SiF_4$, $CCl_3F$, $CClF_2$, $CHF_3$, or $CCl_2FCClF_2$, at elevated temperatures until the desired degree of fluorination is obtained, e.g., at about 200° C. to about 450° C. By vaporizable fluorine-containing fluorinating compound is meant a compound which will convert the alumina component of the instant invention to the desired degree of fluorination using the pretreatment conditions described herein. Such treatments are well known to the art. The treatment with HF or other vaporizable fluorine-containing compound can conveniently be done in the reactor which is to be used for isomerizing the saturated fluorohydrocarbon.

In addition, the invention catalyst composition can also be prepared by co-precipitation of the metal, if any, and the aluminum as hydroxides which are thereafter dried and calcined to form the mixed oxides, a technique well known to the art. The resulting oxide(s), or if desired the aluminum hydroxide itself, is then pretreated with HF as described in Example 1 below.

A suitable catalyst may be prepared, for example, as follows:

A quantity of alumina is dried until essentially all moisture is removed, e.g., for about 18 hours at 100° C. The dried catalyst is then transferred to the reactor to be used. The temperature is gradually increased to about 400° C. while maintaining a flow of $N_2$ through the reactor to remove any remaining traces of moisture from the catalyst and the reactor. The temperature is then lowered to about 200° C., and HF, diluted with $N_2$, is passed through the reactor. The $N_2$ can be gradually reduced until only HF is being passed through the reactor. At this point the temperature can be increased to about 450° C. and held at that temperature to convert the impregnated $Al_2O_3$ to a fluoride content corresponding to at least 50% $AlF_3$ by weight, e.g., for 15 to 300 minutes, depending on the HF flow and the catalyst volume.

A metal containing catalyst may be prepared by impregnating alumina with a solution, usually aqueous, of one or more of the metal compounds described above. The amount of metal expressed as the divalent oxide, will be between about 0.02 to 50 weight percent of the alumina support, preferably not more than 20 weight percent, and more preferably 0.1 to 10 weight percent. The impregnated alumina can be dried until essentially all moisture is removed and treated in the same manner as described above for alumina.

Another suitable procedure for the catalyst preparation is to add ammonium hydroxide to a solution of $Al(NO_3)_3$ and, if present, a metal in the form of a water soluble compound, such as $Ni(NO_3)_2$. The ammonium hydroxide is added to the nitrate solution to a pH of about 8.8. At the end of the addition, the solution is filtered, the solid obtained is washed with water, dried and slowly heated to 500° C., where it is calcined. The calcined product is then treated with a suitable fluorine-containing compound as described above.

The isomerization of the saturated fluorohydrocarbon in the presence of the catalyst of the instant invention is conducted at 200° C. to 475° C., preferably about 300° C. to 450° C. and most preferably about 350° C. to 450° C.

The contact time can vary widely depending on the degree of conversion desired and generally will be about 30 to 180 seconds, preferably about 60 to 90 seconds.

The saturated fluorohydrocarbons may be fed as is or diluted with oxygen or an inert gas such as nitrogen, helium or argon.

In accordance with this invention any mixture of saturated fluorohydrocarbons can be utilized. In practice, for ease of separation, isomerization of one saturated fluorohydrocarbon at a time is recommended. In practice, as the isomerization progresses, both any unreacted saturated fluorohydrocarbon and the resulting isomer can be recycled to the reactor until the desired degree of isomer purity is obtained.

The isomerization of saturated fluorohydrocarbons may be conducted in any suitable reactor, including fixed and fluidized bed reactors. The reaction vessel should be constructed from materials which are resistant to the corrosive effects of the hydrogen fluoride which may be formed in small amounts, such as Hastelloy ® alloy and Inconel ® alloy.

Pressure is not critical. Atmospheric and superatmospheric pressures are the most convenient and are therefore preferred.

The fluorocarbons of this invention are useful as refrigerants, blowing agents, propellants, cleaning agents, solvents, and intermediates for the preparation of other fluorocarbons.

EXAMPLES

In the following illustrative Examples, all parts and percentages are by weight and all temperatures are Celsius. All product compositions are area percent.

General Procedure for Fluorination

The reactor (0.5 inch ID×5" Inconel ® alloy pipe) was charged with alumina, metal compound supported on alumina, or aluminum fluoride, as described in the following examples, and placed in a sand bath. The bath was gradually heated to 400° C. while nitrogen at 50 cc/min was passed through the reactor to remove traces of water.

When the reactor was charged with an alumina support, the temperature was lowered to 200° C., and HF and $N_2$ gas (¼ molar ratio) were passed through the reactor. The $N_2$ flow was decreased with time until neat HF was being passed through the reactor. At this point the temperature was gradually raised to 450° C. and maintained there for 15 to 300 minutes. The fluorine content of the catalyst composition corresponded to an $AlF_3$ content, exclusive of any added metal, of at least 50%.

General Procedure for Isomerization

The temperature was adjusted to the indicated value, followed by the initiation of flow of the fluorohydrocarbon and, optionally, with air or an inert gas. All flows were adjusted to give the indicated molar ratios and contact times in the Examples. The reactor effluent was sampled on-line by a Hewlett Packard 5890 gas chromatograph using a 20 foot×⅛" ID stainless steel column containing Krytox ® perfluorinated polyether on an inert support and with a helium flow of 35 cc/minute. Gas chromatographic conditions were 70° for 3 min followed by temperature programming to 180° C. at a rate of 6° C./min.

EXAMPLE I

Isomerization of $CHF_2CHF_2$

A. $Al(OH)_3$ (38.98 g) was dissolved in 48% aqueous HF (100 mL) in a polyethylene tray. The solution was evaporated at room temperature over 72 h in a fume hood. The resulting white residue was dried at 110° C. for 48 h. The solid was then heated in air at 5° C./min to 500° C. and held at this temperature for 3 h. After cooling, the solid was crushed and sieved to yield 17.47 g of 12 ×20 mesh granule B. The isomerization procedure was followed using the $AlF_3$ catalyst (15.7 g, 25 mL) prepared in . A 1/1 molar ratio mixture of $CHF_2CHF_2$/air was passed over this catalyst at 425° C. with a contact time of 60 seconds. After about 30 minutes of operation a 99.0% conversion of HFC-134 to HFC-134a with a selectivity of 94.6% was observed.

EXAMPLES 2-7

Isomerization of $CHF_2CHF_2$

A. A sample of 1/12" alumina extrudate was dried at 110° C. for 18 h in air. A portion (100 g) of this dried alumina was added to a solution of $LaCl_3.6H_2O$ (12.4 g) and distilled water (175 mL) in a large evaporating dish. The slurry was dried on a hot plate, with occasional stirring for 3 h. The solid was then dried at 110° C. for 18 h in air and treated with HF as described above in the general procedure for fluorination.

B. The isomerization procedure was followed using the above described catalyst (19.1 g, 30 mL) containing 4.9% lanthanum. A ½ molar ratio mixture of $CHF_2CHF_2/N_2$ was passed over this catalyst with a contact time of 60 s. The results are shown Table 1.

TABLE 1

| Ex. | Temp. | % $CHF_2CHF_2$ | % $CF_3CH_2F$ | % $CF_2=CHF$ |
|---|---|---|---|---|
| 2 | 300° C. | 96.0 | 1.9 | — |
| 3 | 350° | 93.2 | 4.5 | — |
| 4 | 375° | 84.2 | 13.3 | — |
| 5 | 400° | 61.9 | 33.4 | 1.7 |
| 6 | 425° | 33.6 | 59.5 | 4.8 |
| 7 | 450° | 21.3 | 68.1 | 9.0 |

EXAMPLES 8-11

Isomerization of $CHF_2CHF_2$

A. A sample of 1/12" alumina extrudate was dried at 110° C. for 18 h in air. A portion (100 g) of this dried alumina was added to a solution of $MnCl_2.4H_2O$ (6.6 g) in distilled water (175 mL) in a large evaporating dish. The slurry was dried on a hot plate, with occasional stirring for 3 h. The solid was then dried at 110° C. for 18 h in air and treated with HF as described above in the general procedure for fluorination.

B. The isomerization procedure was followed using the above prepared catalyst (19.5 g, 30 mL) containing 1.9% manganese. A ½ molar ratio mixture of with a contact $CHF_2CHF_2/N_2$ was passed over this catalyst time of 60 seconds. The results are shown in Table 2.

TABLE 2

| Ex. | Temp. | % $CHF_2CHF_2$ | % $CF_3CH_2F$ | % $CF_2=CHF$ |
|---|---|---|---|---|
| 8 | 350° C. | 96.6 | 0.6 | — |
| 9 | 400° | 87.4 | 7.5 | 0.3 |
| 10 | 430° | 58.6 | 33.8 | 2.0 |
| 11 | 450° | 54.1 | 37.4 | 4.5 |

EXAMPLES 12-13

Isomerization of $CHF_2CHF_2$

A. A sample of 1/12" alumina extrudate was dried at 110° C. for 18 h in air and treated with HF as described above in the general procedure for fluorination.

B. The isomerization procedure was followed using the above prepared catalyst (30 mL). A ½ molar ratio of $CHF_2CHF_2/N_2$ was passed over this catalyst with a contact time of 30 seconds. The results are shown in Table 3.

TABLE 3

| Ex. | Temp. | % $CHF_2CHF_2$ | % $CF_3CH_2F$ | % $CF_2=CHF$ |
|---|---|---|---|---|
| 12 | 350° C. | 62.5 | 33.5 | 1.5 |
| 13 | 400° | 59.3 | 35.0 | 3.2 |

EXAMPLE 14

Isomerization of $CHF_2CHF_2$

A. A sample of 1/12" alumina extrudate was dried at 110° C. for 18 h and treated with HF as described above in the general procedure for fluorination.

B. The isomerization procedure was followed using the above prepared catalyst (30 mL). A ½/.2 molar ratio mixture of $CHF_2CHF_2/N_2/O_2$ was passed over this catalyst at 400° C. with a contact time of 60 seconds. After 7.3 hours on-line, the product stream contained 86.5% HFC-134, 10.3% HFC-134a, and 1.8% $CF_2=CHF$.

We claim:

1. A process for isomerizing saturated $C_2$ to $C_6$ fluorohydrocarbons having lesser thermodynamic stability to fluorohydrocarbons having greater thermodynamic stability comprising;
   contacting in the gaseous phase at a temperature from about 200° C. to about 475° C. at least one $C_2$ to $C_6$ saturated fluorohydrocarbon with a catalyst composition comprising an aluminum fluoride.

2. The process of claim 1 wherein the saturated fluorohydrocarbon having lesser thermodynamic stability is selected from at least one of 1,1,2,2-tetrafluoroethane, 1,1,2-trifluoroethane and 1,2-difluoroethane.

3. The process of claim 2 wherein the saturated fluorohydrocarbon having lesser thermodynamic stability is 1,1,2,2-tetrafluoroethane.

4. The process of claim 1 wherein the isomer of the saturated fluorohydrocarbon having greater thermodynamic stability is selected from at least one of 1,1,1,2-tetrafluoroethane, 1,1,1-trifluoroethane and 1,1-difluoroethane.

5. The process of claim 4 wherein the isomer of the saturated fluorohydrocarbon having greater thermodynamic stability is 1,1,1,2-tetrafluoroethane.

6. The process of claim 1 wherein the aluminum fluoride is selected from at least one of $AlF_3$ and fluorided alumina.

7. The process of claim 6 wherein the fluorided alumina is a high fluorine-content composition comprising aluminum, oxygen, and fluorine in such proportions that the total fluorine content of the catalyst composition taken as $AlF_3$ is at least 50 weight percent.

8. The process of claim 1 wherein the catalyst composition comprises up to 50% by weight of at least one metal on a support consisting essentially of aluminum, oxygen, and fluorine in such proportions that the fluorine content of the catalyst composition corresponds to an $AlF_3$ content of at least 50% by weight of the catalyst composition exclusive of the metal.

9. The process of claim 1 wherein the temperature is from about 300° C. to about 450° C.

10. The process of claim 1 wherein the temperature is from about 350° C. to about 450° C.

11. The process of claim 1 wherein the catalyst composition is treated with a vaporizable fluorine-containing fluorinating compound at a temperature from about 200° C. to about 450° C. until the fluorine content of the catalyst composition corresponds to an $AlF_3$ content of at least 50% by weight of the catalyst composition.

12. The process of claim 1 wherein the contacting is conducted in the presence of an oxygen-containing gas.

* * * * *